US012741972B2

(12) United States Patent
Xu et al.

(10) Patent No.: US 12,741,972 B2
(45) Date of Patent: Sep. 22, 2026

(54) METHOD FOR CARRYING OUT REACTION OF ISATIN COMPOUND AND CYCLOPROPENONE COMPOUND AT LOW CATALYTIC AMOUNT

(71) Applicant: SOOCHOW UNIVERSITY, Suzhou (CN)

(72) Inventors: Fan Xu, Suzhou (CN); Qifa Chen, Suzhou (CN); Yue Teng, Suzhou (CN); Zhigang Yao, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 428 days.

(21) Appl. No.: 18/037,556

(22) PCT Filed: Mar. 10, 2021

(86) PCT No.: PCT/CN2021/080091
§ 371 (c)(1),
(2) Date: Nov. 26, 2023

(87) PCT Pub. No.: WO2022/188082
PCT Pub. Date: Sep. 15, 2022

(65) Prior Publication Data

US 2024/0109908 A1 Apr. 4, 2024

(51) Int. Cl.
*C07D 491/052* (2006.01)
*B01J 31/18* (2006.01)
*B01J 31/22* (2006.01)

(52) U.S. Cl.
CPC ...... *C07D 491/052* (2013.01); *B01J 31/1805* (2013.01); *B01J 31/2208* (2013.01); *B01J 2231/48* (2013.01); *B01J 2531/0205* (2013.01); *B01J 2531/11* (2013.01); *B01J 2531/37* (2013.01); *B01J 2531/38* (2013.01)

(58) Field of Classification Search
CPC .............. C07D 491/052; B01J 31/1805; B01J 31/2208; B01J 2231/48; B01J 2531/0205; B01J 2531/11; B01J 2531/37; B01J 2531/38
See application file for complete search history.

(56) References Cited

FOREIGN PATENT DOCUMENTS

| | | | |
|---|---|---|---|
| CN | 106423281 A | | 2/2017 |
| CN | 106432052 A | | 2/2017 |
| WO | 106432052 | * | 2/2017 |

OTHER PUBLICATIONS

Lu Wang et al., "Lanthanide Amides [(Me3Si)2N]3Ln(μ-Cl)Li(THF)3-Catalyzed Phospho-Aldol-Brook Rearrangement Reaction of Dialkyl Phosphites with Isatins" Heteroatom Chemistry, vol. 23, No. 5, 2012, pp. 449-456 (Dec. 31, 2012).
Junyu Xu et al., "Organocatalytic C—C bond activation of cyclopropenones for ring-opening formal [3 + 2] cycloaddition with isatins" Org. Chem. Front., 2017, 4, 560 (Jan. 16, 2017).

* cited by examiner

*Primary Examiner* — Brandon J Fetterolf
(74) *Attorney, Agent, or Firm* — SZDC Law PC

(57) ABSTRACT

A method for the reaction of an isatin and cyclopropenone compound at low catalytic amount. In the presence of an amine compound and phosphite, the isatin and cyclopropenone are reacted in an organic solvent using a silicon amino rare earth compound as a catalyst to synthesize pyrano[2,3-b]indol-2-one compounds. In the reaction above, the amount of catalyst is few, and noble metal is not needed for catalysis. The present method can achieve preparation of the pyrano[2,3-b]indol-2-one compound efficiently and simply.

7 Claims, No Drawings

METHOD FOR CARRYING OUT REACTION OF ISATIN COMPOUND AND CYCLOPROPENONE COMPOUND AT LOW CATALYTIC AMOUNT

This application is the National Stage Application of PCT/CN2021/080091, filed on Mar. 10, 2021, which is incorporated by reference for all purposes as if fully set forth herein.

TECHNICAL FIELD

The present invention belongs to the field of preparation technology for fused heterocycles, and specifically relates to a method for the reaction of isatin and cyclopropenone compound at low catalytic amount.

BACKGROUND OF INVENTION

The pyrano[2,3-b]indol-2-one skeleton contains pyran and indole, and is one of the most important constitutional units in pharmaceutical chemistry. For example, the following pyrano[2,3-b]indol-2-one skeleton compound that has been proven to have practical medicinal properties includes:

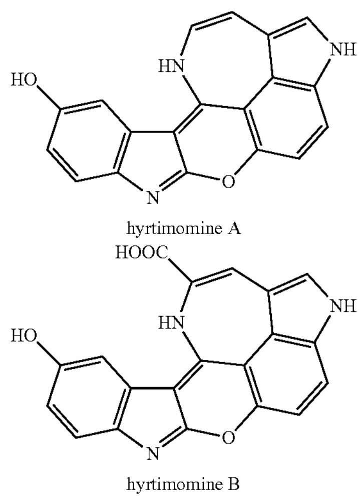
hyrtimomine A hyrtimomine B

There are different methods for preparing pyrano[2,3-b]indol-2-one skeleton in the prior art, such as:

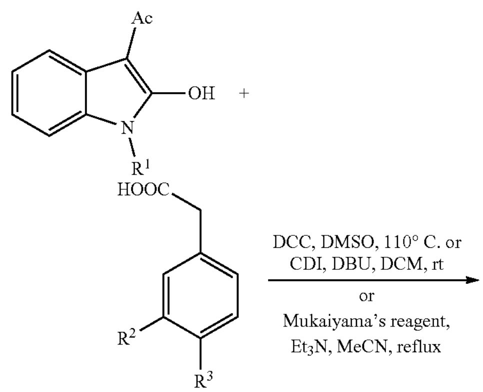

-continued

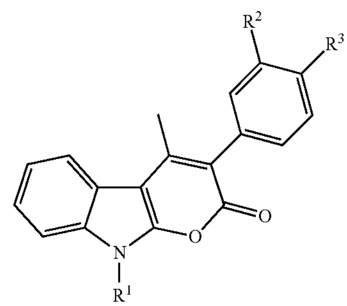

The existing methods can synthesize pyrano[2,3-b]indol-2-one compounds, but they all have some defects, such as low yield, cumbersome synthesis steps, complex substrate structure, and the need for precious metal catalysts, etc.

In addition, in view of catalytic synthesis schemes, the amount of catalyst needs to be minimized as much as possible, which is beneficial for reaction cost, reaction stability, and product purification.

Technical Problems

The present invention discloses the reaction of isatin catalyzed by a small amount of silicon amino rare earth compound and cyclopropenone compound and a method for synthesizing pyrano[2,3-b]indol-2-one compound with simple raw material sources, simple steps, mild reaction conditions, high activity, and good universality through the reaction of isatin catalyzed by the silicon amino rare earth compound, phosphite ester, and cyclopropenone compound.

Technical Solution

In order to achieve the above invention objective, the technical scheme adopted by the present invention is a method for reacting isatin with cyclopropenone compound at low catalytic amount, comprising the following steps: the silicon amino rare earth compound are used as catalysts for reacting isatin with cyclopropenone in an organic solvent in the presence of amine compound and phosphite ester.

The application of amine compound and silicon amino rare earth compound in the reaction of a isatin and cyclopropenone compound.

The isatin of the present invention reacts with cyclopropenone under anhydrous and anaerobic conditions, and the product of the reaction between the isatin and cyclopropenone is a pyrano[2,3-b]indol-2-one compound.

In the invention, chemical structural formula of the amine compound is as follows:

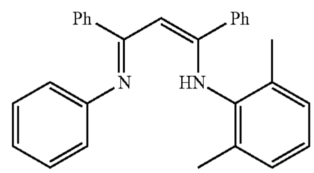 [SMILES: Cc1cccc(C)c1N/C(=C\C(=N\c1ccccc1)c1ccccc1)c1ccccc1]

The chemical structural formula of silicon amino rare earth compound is as follows:

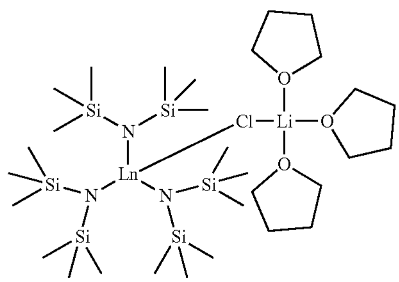

Wherein: Ln is a trivalent rare earth metal ion.

The general structure of the isatin is as follows:

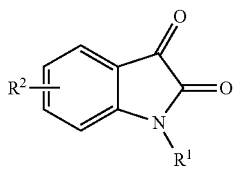

The general structure of the cyclopropenone is as follows:

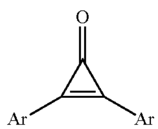

The chemical structural formula of pyrano[2,3-b]indol-2-one compound is as follows:

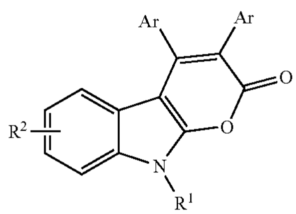

In the above structural formula, $R^1$ is selected from one of allyl, benzyl, ethyl, methyl, or acetyl; $R^2$ is selected from one of chlorine, fluorine, bromine, methyl, methoxy, nitro, trifluoromethyl, or trifluoromethoxy; Ar is selected from one of phenyl, 4-methylphenyl, 4-fluorophenyl, and 4-chlorophenyl.

The chemical formula of the catalyst of the present invention is $[(Me_3Si)_2N]_3Ln(\mu\text{-}Cl)Li(THF)_3$, wherein: $(Me_3Si)_2N$ represents trimethylsilylamide, Ln represents a trivalent rare earth metal ion, selected from one of lanthanum, neodymium, samarium, erbium, or ytterbium, preferably lanthanum (La). Under the same conditions, its catalytic reaction yields higher output of pyrano[2,3-b]indol-2-one compound compared to the other four metals; μ-represents bridged bond; and THF represents tetrahydrofuran.

In the present invention, the phosphite ester is diethyl phosphite; the anhydrous and anaerobic condition is preferred to be in an inert atmosphere.

In the above technical solution, the reaction is carried out in an organic solvent, which is one of 1,4-dioxane, ethylene glycol dimethyl ether, tetrahydrofuran, 1,2-dichloroethane, chlorobenzene, toluene, and n-hexane; and toluene is preferred. Under the same conditions, the yield in toluene is significantly higher than that in other solvents, achieving significant technological effect.

In the above technical solution, the reaction temperature is at range from 100° C. to 120° C., preferably 110° C.; the reaction time is for 2-3 hours, preferably 2.5 hours.

In the above technical solution, the amount of the catalyst is 10% of the mole number of cyclopropenone; and the molar ratio of the catalyst to the amine compound is 1:3, preferably 1:1. The amount of catalyst used in the present invention is low, which ensures efficient reaction while avoiding increased reaction costs and simplifying the post-treatment of the reaction system.

In the above technical solution, the amount of diethyl phosphite is range from 1 time to 1.5 times the mole number of cyclopropenone; and the preferred amount of phosphite ester is 1.2 times the molar weight of cyclopropenone; the amount of diethyl phosphite in the present invention is beneficial for the complete reaction, while avoiding waste caused by the incomplete reaction of diethyl phosphite, and is also beneficial for post-treatment.

In the above technical solution, the amount of isatin is range from 1 time to 1.5 times the mole number of cyclopropenone; and the preferred amount of isatin is 1.2 times the molar weight of cyclopropenone; the amount of isatin in the present invention is beneficial for improving the reaction efficiency and avoiding waste and is also beneficial for post-treatment.

In the above technical solution, the reaction process includes mixing silicon amino rare earth compound and amine compound in a solvent under anhydrous and anaerobic condition; then phosphite ester, isatin compound, and solvent are added and mixed, and then cyclopropenone and the solvent are added for reaction in a pot. After the reaction is terminated, the extraction is carried out and the extraction solution is dried with desiccant and filtered, and the solvent is removed under reduced pressure. Finally, the pyrano[2,3-b]indol-2-one compound is obtained through flash column chromatography. In the preferred technical solution, water is used to terminate the reaction, the extractant is ethyl acetate, the desiccant is anhydrous sodium sulfate, and the eluent is the ethyl acetate/petroleum ether system (volume ratio is 1:10).

The above technical solution can be expressed as follows:

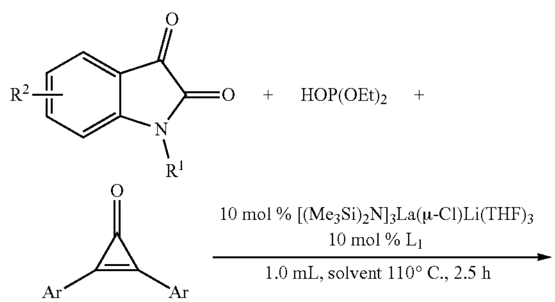

-continued

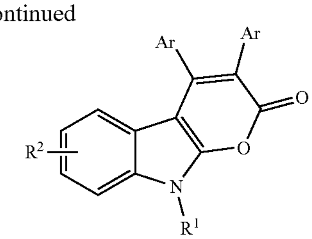

Beneficial Effects

Due to the application of the above technical solution, the present invention has the following advantages compared to existing technologies:

1. For the first time, the present invention uses a silicon amino rare earth compound $[(Me_3Si)_2N]_3Ln(\mu\text{-}Cl)Li(THF)_3$ as catalyst for the preparation of pyrano[2,3-b]indol-2-one compound through the reaction of isatin compound, phosphite ester, and cyclopropenone at a molar weight of 10% in the presence of amine compound. The raw materials are simple and easy to obtain, and the yield of the target product is high, reaching a maximum of 91%.
2. The synthetic route disclosed in the present invention adopts a one-pot reaction method, which adds catalyst, amine compound, isatin compound, phosphite ester, and cyclopropenone to a solvent for one-pot reaction. The amount of catalyst used is small, the reaction time is short, and the product yield is high, overcoming the defects of cumbersome reaction steps and low yield in the prior art.
3. The method disclosed in the present invention does not use precious metal catalysts, has low catalyst amount, low reaction cost, and is also beneficial for protecting the environment; At the same time, the catalyst synthesis method used in the present invention is simple, with high yield, and the entire process of preparing pyrano[2,3-b]indol-2-one compound is controllable.

EXAMPLES OF THE PRESENT INVENTION

The present invention uses isatin compound, phosphite ester, and cyclopropenone as reactants, and silicon amino rare earth compound as catalyst to prepare pyrano[2,3-b]indol-2-one compounds in the presence of amine compound in an organic solvent under anhydrous and anaerobic conditions. It doesn't need other reagents and other reaction steps, and the reaction materials are mixed, for reaction to obtain the product of the present invention. After conventional purification, the purified product is obtained with simple steps.

The raw materials of the present invention are all existing products, and the specific operating and testing methods are conventional methods in the field. Unless otherwise specified, they are all carried out under conventional conditions. The following is a further description of the present invention in conjunction with an Example: Synthesis Example 1: Synthesis of catalyst $[(Me_3Si)_2N]_3La(\mu\text{-}Cl)Li(THF)_3$: n-buLi hexane solution (60 mmol, 2.52M) was drop wise added to a 100 mL Schlenk reaction flask containing $(Me_3Si)_2NH$ (60 mmol) at −10° C., and the reaction was carried out at room temperature for 30 minutes. The above reaction solution was added to the anhydrous $LaCl_3$ (20 mmol) THF (30 mL) suspension and stirred overnight at room temperature. The solvent was removed under reduced pressure to Cl) Li obtain the solid powder, which was extracted with hot toluene to remove LiCl, concentrated and placed at 0° C. to precipitate a large number of crystals, which were the desired aminosilylation lanthanum compound with a yield of 85%.

For the other catalysts, the preparation method of Example 1 can be used as reference.

Synthesis Example 2: Synthesis of Amine Compound $L_1$ and Amine Compound $L_2$

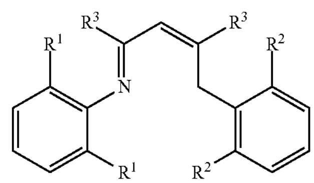

$R^1 = H, R^2 = CH_3, R^3 = Ph, L_1$
$R^1, R^2 = CH_3, R^3 = CH_3, L_2$

The aniline (1.82 mL, 20 mmol) and 1,3-diphenyl-1,3-dione (5.38 g, 24 mmol) were mixed in 80 mL of toluene, and then p-toluenesulfonic acid (0.35 g, 2 mmol) was added. The mixture was refluxed with an oil-water separator to remove water for 24 hours and cooled. The solvent was removed under reduced pressure, and the residue was separated using a silica gel column (eluent: ethyl acetate:petroleum ether=1:60) to obtain a yellow solid. The yellow solid was mixed with 2,6-dimethylaniline hydrochloride (1.77 g, 11.2 mmol) in 50 mL of ethanol and reflux for 48 hours. Then it was cooled and filtered. After the filtrate was concentrated, ethanol and water were added, neutralized with a sodium hydroxide aqueous solution, and extracted with ether. The obtained organic phase was dried with anhydrous sodium sulfate, the solvent was removed under reduced pressure, and a yellow solid was obtained using a silica gel column, which was the desired $L_1$ with a yield of 10%. The main nuclear magnetic testing data are as follows: $^1H$ NMR (400 MHz, $CDCl_3$) δ: 12.90 (s, 1H), 7.45-7.43 (m, 2H), 7.31-7.16 (m, 8H), 7.07 (t, J=7.7 Hz, 2H), 6.92-6.80 (m, 4H), 6.70 (d, J=7.8 Hz, 2H), 5.42 (s, 1H), 2.10 (s, 6H).

2,6-dimethylaniline (20 g, 0.17 mol), 2,4-pentanedione (8.25 g, 0.08 mol), and p-toluenesulfonic acid (14.2 g, 0.08 mol) were mixed in 250 mL of toluene and reflux for 24 hours. Toluene was poured out and 200 mL of ether, 150 mL of water, and 36 g of sodium carbonate decahydrate were added to the solid residue, and stirred for 25 min. The separated ether layer was dried with magnesium sulfate and the solvent was removed under reduced pressure. The residue was vacuum dried at 100° C. for 6 hours to obtain the required solid $L_2$ with a yield of 70%. The main nuclear magnetic testing data are as follows: $^1H$ NMR (400 MHz, $CDCl_3$) δ: 12.25 (s, 1H), 7.09-6.97 (m, 6H), 4.93 (s, 1H), 2.21 (s, 12H), 1.74 (s, 6H).

Example: the preparation of pyrano[2,3-b]indol-2-one compound with $[(Me_3Si)_2N]_3La(\mu\text{-}Cl)Li(THF)_3$ catalyzed N-ethyl isatin, diethyl phosphite and diphenylcyclopropenone: at room temperature, $[(Me_3Si)_2N]_3La(\mu\text{-}Cl)Li(THF)_3$ (21.1 mg, 0.024 mmol, 10 mol %), $L_1$ (9.7 mg, 0.024 mmol) and toluene (0.1 mL) were weighed into a reaction flask after dehydration and deoxygenation treatment under argon protection for conventional mixing for 10 minutes, then diethyl phosphite (Compound 2, 37 μL, 0.29 mmol), isatin (N-ethyl isatin, 0.29 mmol) and toluene (0.3 mL) were added for conventional stirring and mixing for 30 min, and then toluene (0.6 mL) and 2,3-diphenylcyclohexanone (Compound 3, 50 mg, 0.24 mmol) were added and stirred at 110° C. for 2.5 h, and water was added to terminate the reaction. After that, it was extracted with ethyl acetate for three times, and the extract was dried with anhydrous sodium sulfate, filtered, and the solvent was removed under reduced pressure. Finally, a yellow solid product was obtained through rapid column chromatography with a silica gel column (eluent: ethyl acetate:petroleum ether=1:10), with a yield of 88%; the theoretical molecular formula and main nuclear magnetic testing data of the prepared product were as follows. Through analysis, it could be seen that the actual synthesized product is consistent with the theoretical analysis.

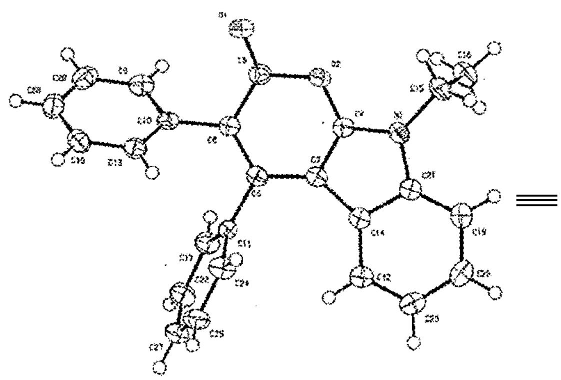

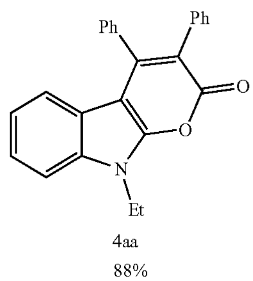

4aa

88%

$^1$H NMR (400 MHz, $CDCl_3$) δ: 7.36-7.31 (m, 4H), 7.25-7.21 (m, 3H), 7.19-7.10 (m, 5H), 7.00-6.96 (m, 1H), 6.78 (d, J=8.0 Hz, 1H), 4.35 (q, J=7.2 Hz, 2H), 1.50 (t, J=7.2 Hz, 3H).

The isatin (Compound 1: 0.29 mmol) was changed with the remaining conditions keeping unchanged. The prepared product, pyrano[2,3-b]indol-2-one compound (Compound 4), and the separation yield are as follows.

4ba

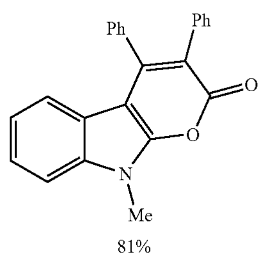

81%

-continued

4ca

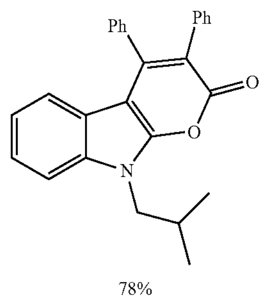

78%

4da

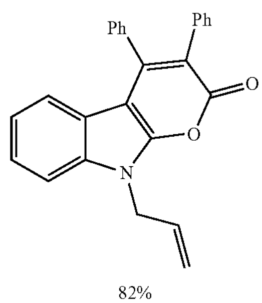

82%

4ea

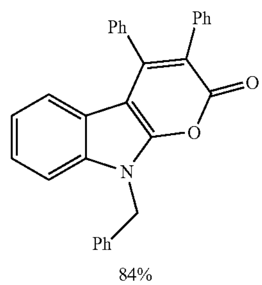

84%

4fa

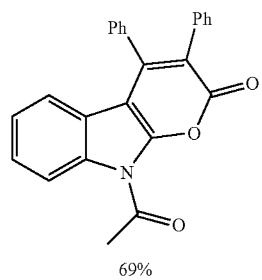

69%

4ga

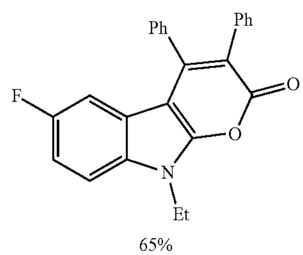

65%

-continued
4ha
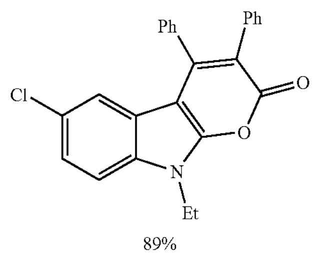
89%
4ia
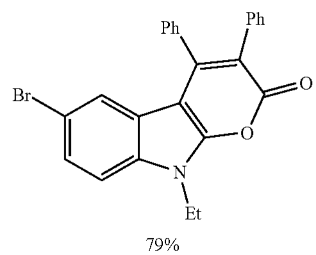
79%
4ja
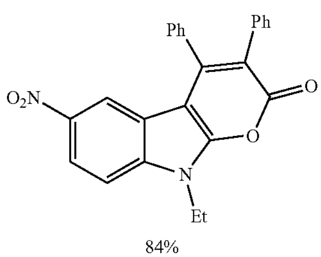
84%
4ka
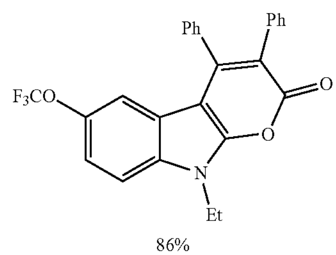
86%
4la
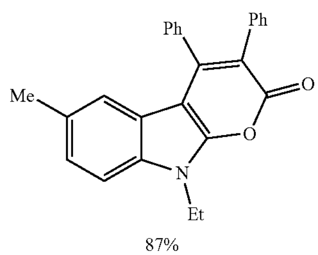
87%
4ma
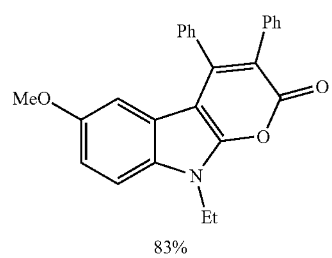
83%
-continued
4na
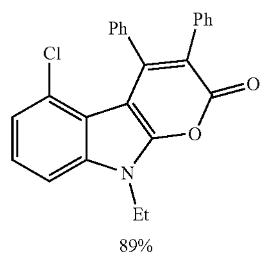
89%
4oa
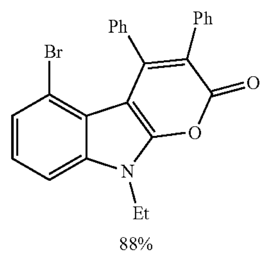
88%
4pa
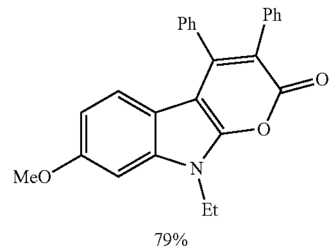
79%
4qa
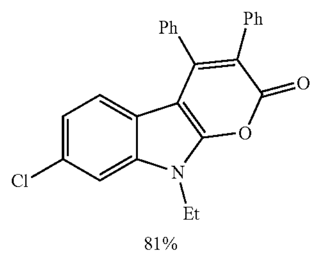
81%
4ra
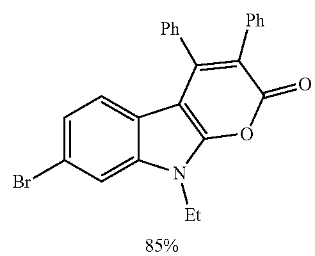
85%
4sa
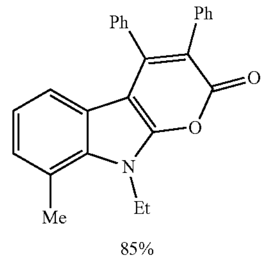
85%

-continued
4ta
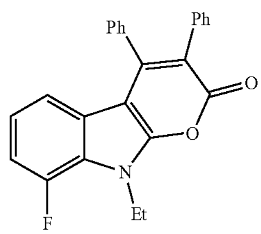
88%
4ua
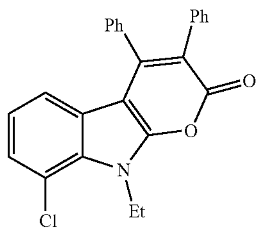
84%
4va
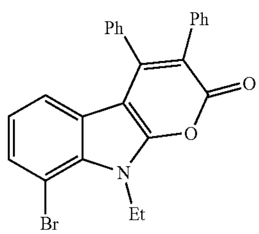
80%
4wa
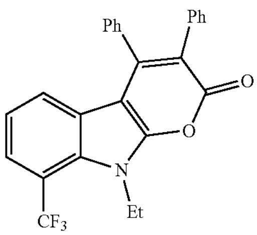
74%
4xa
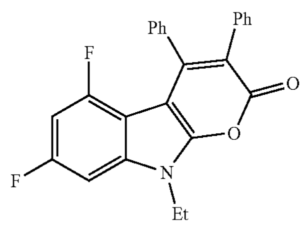
91%
4ya
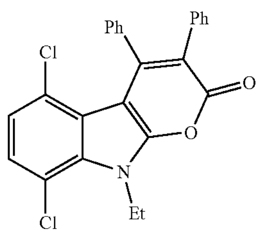
89%
The 2,3-diphenylcyclohexanone (Compound 3, 0.24 mmol) was changed with the remaining conditions keeping unchanged. The prepared product, pyrano[2,3-b]indol-2-one compound (Compound 4), and the separation yield are as follows.
4ab
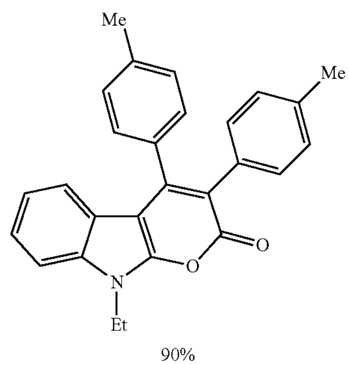
90%
4ac
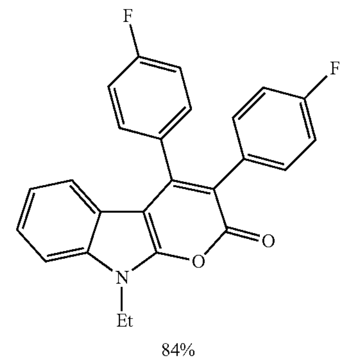
84%
4ad
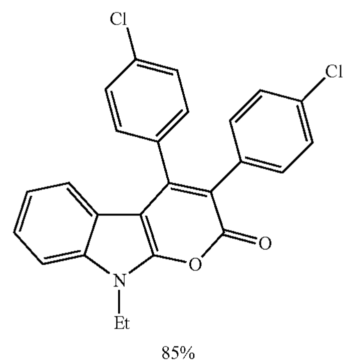
85%
The above reaction process is as follows.
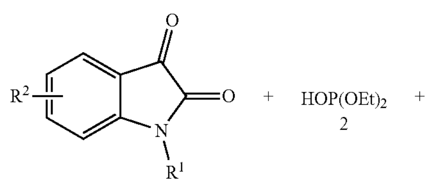
1
2

-continued

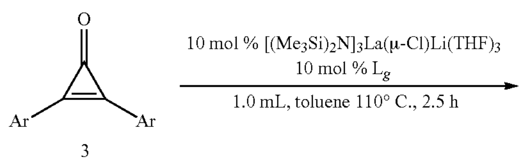

3

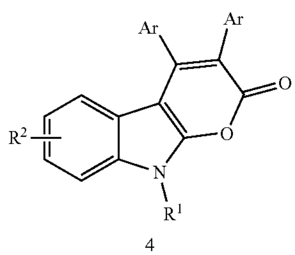

4

The theoretical molecular formulas and main nuclear magnetic testing data of some of the products obtained are as follows:

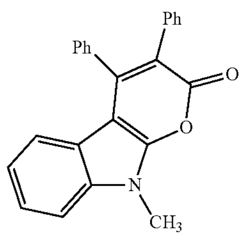 [SMILES: Cn1c2ccccc2c2c(-c3ccccc3)c(-c3ccccc3)c(=O)oc21]

$^1H$ NMR (400 MHz, $CDCl_3$) δ: 7.33-7.30 (m, 4H), 7.24-7.20 (m, 3H), 7.19-7.12 (m, 5H), 7.02-6.98 (m, J=8.0 Hz, 1H), 6.78 (d, J=8.0 Hz, 1H), 3.82 (s, 3H).

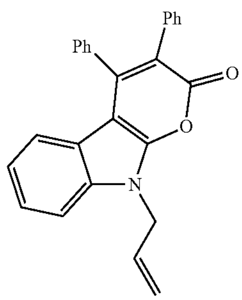 [SMILES: C=CCn1c2ccccc2c2c(-c3ccccc3)c(-c3ccccc3)c(=O)oc21]

$^1H$ NMR (400 MHz, $CDCl_3$) δ: 7.34-7.32 (m, 4H), 7.25-7.13 (m, 8H), 7.01-6.97 (m, 1H), 6.78 (d, J=7.6 Hz, 1H), 6.05-5.96 (m, 1H), 5.30-5.20 (m, 2H), 4.91 (d, J=5.2 Hz, 2H).

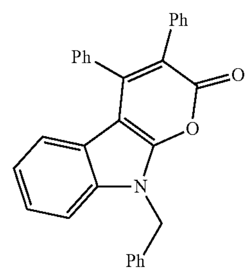 [SMILES: O=c1oc2c(c(-c3ccccc3)c1-c1ccccc1)c1ccccc1n2Cc1ccccc1]

$^1H$ NMR (400 MHz, $CDCl_3$) δ: 7.35-7.24 (m, 11H), 7.21-7.12 (m, 6H), 7.00-6.96 (m, 1H), 6.78 (d, J=8.0 Hz, 1H), 5.50 (s, 2H).

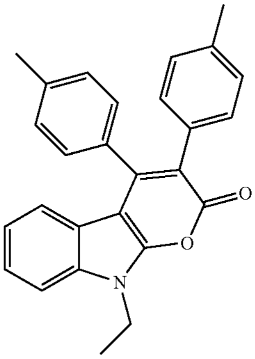 [SMILES: CCn1c2ccccc2c2c(-c3ccc(C)cc3)c(-c3ccc(C)cc3)c(=O)oc21]

$^1H$ NMR (400 MHz, $CDCl_3$) δ: 7.35 (d, J=8.4 Hz, 1H), 7.25-7.21 (m, 1H), 7.16-7.11 (m, 4H), 7.05-6.98 (m, 5H), 6.84 (d, J=8.0 Hz, 1H), 4.35 (q, J=7.2 Hz, 2H), 2.37 (s, 3H), 2.26 (s, 3H), 1.50 (t, J=7.2 Hz, 3H).

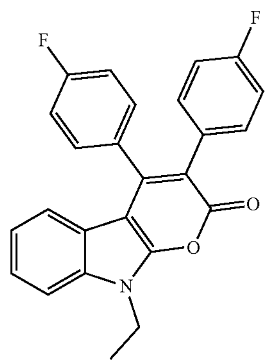 [SMILES: CCn1c2ccccc2c2c(-c3ccc(F)cc3)c(-c3ccc(F)cc3)c(=O)oc21]

$^1H$ NMR (400 MHz, $CDCl_3$) δ: 7.38 (d, J=8.0 Hz, 1H), 7.28-7.19 (m, 3H), 7.12-7.01 (m, 5H), 6.92-6.87 (m, 2H), 6.82 (d, J=8.0 Hz, 1H), 4.36 (q, J=7.2 Hz, 2H), 1.52 (t, J=7.2 Hz, 3H).

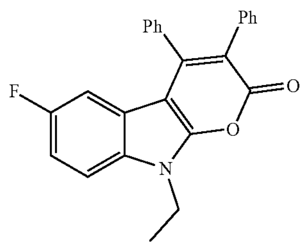 [SMILES: CCn1c2ccc(F)cc2c2c(-c3ccccc3)c(-c3ccccc3)c(=O)oc21]

$^1H$ NMR (400 MHz, $CDCl_3$) δ: 7.33-7.31 (m, 3H), 7.28-7.24 (m, 1H), 7.22-7.11 (m, 7H), 6.97-6.92 (m, 1H), 6.45-6.42 (m, 1H), 4.33 (q, J=7.2 Hz, 2H), 1.50 (t, J=7.2 Hz, 3H).

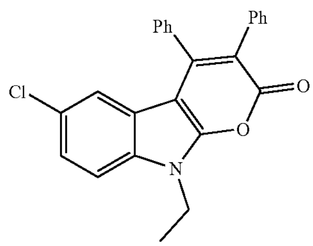 [SMILES: CCn1c2ccc(Cl)cc2c2c(-c3ccccc3)c(-c3ccccc3)c(=O)oc21]

$^1H$ NMR (400 MHz, $CDCl_3$) δ: 7.35-7.33 (m, 3H), 7.25-7.24 (m, 1H), 7.22-7.12 (m, 8H), 6.72 (d, J=2.0 Hz, 1H), 4.33 (q, J=7.2 Hz, 2H), 1.49 (t, J=7.2 Hz, 3H).

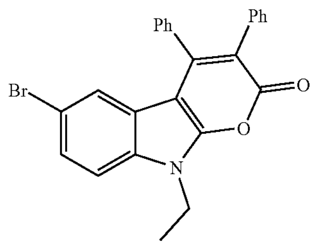 [SMILES: CCn1c2ccc(Br)cc2c2c(-c3ccccc3)c(-c3ccccc3)c(=O)oc21]

$^1H$ NMR (400 MHz, $CDCl_3$) δ: 7.37-7.31 (m, 4H), 7.24-7.13 (m, 8H), 6.87 (d, J=2.0 Hz, 1H), 4.34 (q, J=7.2 Hz, 2H), 1.50 (t, J=7.2 Hz, 3H).

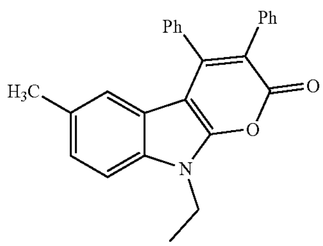 [SMILES: CCn1c2ccc(C)cc2c2c(-c3ccccc3)c(-c3ccccc3)c(=O)oc21]

$^1H$ NMR (400 MHz, $CDCl_3$) δ: 7.35-7.31 (m, 3H), 7.25-7.21 (m, 3H), 7.19-7.11 (m, 5H), 7.07-7.04 (m, 1H), 6.56-6.55 (m, 1H), 4.33 (q, J=7.2 Hz, 2H), 2.23 (s, 3H), 1.49 (t, J=

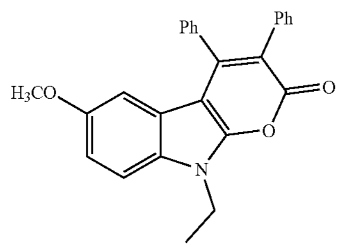 [SMILES: CCn1c2ccc(OC)cc2c2c(-c3ccccc3)c(-c3ccccc3)c(=O)oc21]

$^1H$ NMR (400 MHz, $CDCl_3$) δ: 7.35-7.32 (m, 3H), 7.25-7.22 (m, 3H), 7.18-7.11 (m, 5H), 6.86-6.83 (m, 1H), 6.22 (d, J=2.4 Hz, 1H), 4.31 (q, J=7.2 Hz, 2H), 3.53 (s, 3H), 1.49 (t, J=7.2 Hz, 3H).

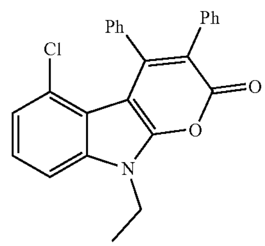 [SMILES: CCn1c2cccc(Cl)c2c2c(-c3ccccc3)c(-c3ccccc3)c(=O)oc21]

$^1H$ NMR (400 MHz, $CDCl_3$) δ: 7.29-7.27 (m, 111), 7.18-7.15 (m, 5H), 7.14-7.09 (m, 4H), 7.07-7.04 (m, 3H), 4.39 (q, J=7.2 Hz, 2H), 1.51 (t, J=7.2 Hz, 3H).

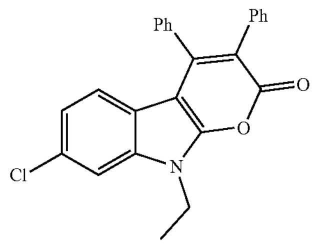 [SMILES: CCn1c2cc(Cl)ccc2c2c(-c3ccccc3)c(-c3ccccc3)c(=O)oc21]

$^1H$ NMR (400 MHz, $CDCl_3$) δ: 7.39-7.34 (m, 4H), 7.26-7.17 (m, 7H), 7.00-6.97 (m, 1H), 6.71 (d, J=8.4 Hz, 1H), 4.36 (q, J=7.2 Hz, 2H), 1.55 (t, J=7.2 Hz, 3H).

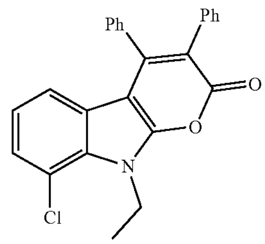 [SMILES: CCn1c2oc(=O)c(-c3ccccc3)c(-c3ccccc3)c2c2cccc(Cl)c21]

$^1H$ NMR (400 MHz, $CDCl_3$) δ: 7.34-7.32 (m, 3H), 7.21-7.14 (m, 8H), 6.87-6.84 (m, 1H), 6.61 (d, J=7.6 Hz, 1H), 4.76 (q, J=7.2 Hz, 2H), 1.55 (t, J=7.2 Hz, 3H).

Extended Example 1: at room temperature, $[(Me_3Si)_2N]_3La$ (μ-Cl)$Li(THF)_3$ (211 mg, 0.24 mmol, 10 mol %), $L_1$ (97 mg, 0.24 mmol) and toluene (0.1 mL) were weighed into a reaction flask after dehydration and deoxygenation treatment under argon protection for conventional mixing for 10 minutes, then diethyl phosphite (2.9 mmol), N-ethyl isatin (2.9 mmol) and toluene (3 mL) were added for conventional stirring and mixing for 30 min, and then toluene (6 mL) and 2,3-diphenylcyclohexanone (2.4 mmol) were added and stirred at 110° C. for 2.5 h, and water was added to terminate the reaction. After that, it was extracted with ethyl acetate for three times, and the extract was dried with anhydrous sodium sulfate, filtered, and the solvent was removed under reduced pressure. Finally, a yellow solid product was obtained through rapid column chromatography with a silica gel column (eluent: ethyl acetate:petroleum ether=1:10), with a yield of 68%; the theoretical molecular formula and main nuclear magnetic testing data of the prepared product were as follows. Through analysis, it could be seen that the actual synthesized product is consistent with the theoretical analysis.

Reaction time 2.5 hours was adjusted to 5 hours, and the rest remained unchanged to obtain product 0.665 g, yield 76%; as follows:

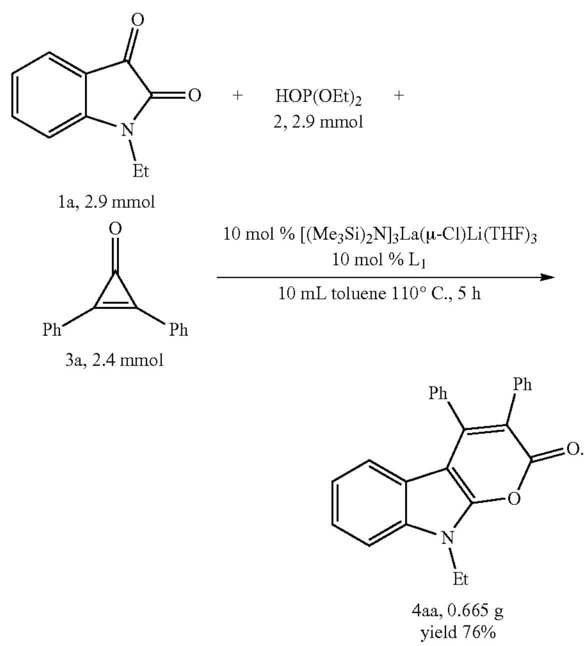

Extended Example 2: at room temperature, $[(Me_3Si)_2N]_3La(\mu\text{-}Cl)Li(THF)_3$ (21.1 mg, 0.024 mmol, 10 mol %), $L_1$ (28.9 mg, 0.072 mmol) and toluene (0.1 mL) were weighed into a reaction flask after dehydration and deoxygenation treatment under argon protection for conventional mixing for 10 minutes, then diethyl phosphite (Compound 2, 37 μL, 0.29 mmol), isatin (N-ethyl isatin, 0.29 mmol) and toluene (0.3 mL) were added for conventional stirring and mixing for 30 min, and then toluene (0.6 mL) and 2,3-diphenylcyclohexanone (Compound 3, 50 mg, 0.24 mmol) were added and stirred at 110° C. for 2.5 h, and water was added to terminate the reaction. After that, it was extracted with ethyl acetate for three times, and the extract was dried with anhydrous sodium sulfate, filtered, and the solvent was removed under reduced pressure. Finally, a yellow solid product was obtained through rapid column chromatography with a silica gel column (eluent: ethyl acetate:petroleum ether=1:10), with a yield of 85%; the theoretical molecular formula and main nuclear magnetic testing data of the prepared product were as follows. Through analysis, it could be seen that the actual synthesized product is consistent with the theoretical analysis.

Control

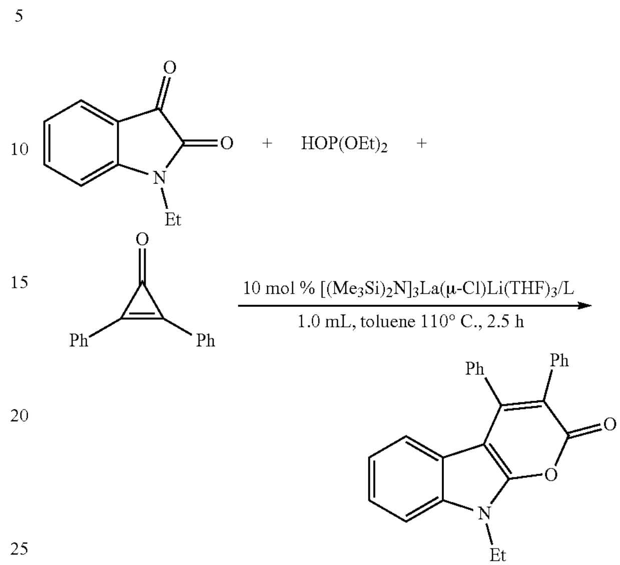

At room temperature, $[(Me_3Si)_2N]_3La(\mu\text{-}Cl)Li(THF)_3$ (21.1 mg, 0.024 mmol, 10 mol %), $L_2$ (7.3 mg, 0.024 mmol) and toluene (0.1 mL) were weighed into a reaction flask after dehydration and deoxygenation treatment under argon protection for conventional mixing for 10 minutes, then diethyl phosphite (Compound 2, 37 μL, 0.29 mmol), isatin (N-ethyl isatin, 0.29 mmol) and toluene (0.3 mL) were added for conventional stirring and mixing for 30 min, and then toluene (0.6 mL) and 2,3-diphenylcyclohexanone (Compound 3, 50 mg, 0.24 mmol) were added and stirred at 110° C. for 2.5 h, and water was added to terminate the reaction. After that, it was extracted with ethyl acetate for three times, and the extract was dried with anhydrous sodium sulfate, filtered, and the solvent was removed under reduced pressure. Finally, a yellow solid product was obtained through rapid column chromatography with a silica gel column (eluent: ethyl acetate:petroleum ether=1:10), with a yield of 55%; the theoretical molecular formula and main nuclear magnetic testing data of the prepared product were as follows. Through analysis, it could be seen that the actual synthesized product is consistent with the theoretical analysis.

At room temperature, $[(Me_3Si)_2N]_3La(\mu\text{-}Cl)Li(THF)_3$ (21.1 mg, 0.024 mmol, 10 mol %), $L_2$ (22.0 mg, 0.072 mmol) and toluene (0.1 mL) were weighed into a reaction flask after dehydration and deoxygenation treatment under argon protection for conventional mixing for 10 minutes, then diethyl phosphite (Compound 2, 37 μL, 0.29 mmol), isatin (N-ethyl isatin, 0.29 mmol) and toluene (0.3 mL) were added for conventional stirring and mixing for 30 min, and then toluene (0.6 mL) and 2,3-diphenylcyclohexanone (Compound 3, 50 mg, 0.24 mmol) were added and stirred at 110° C. for 2.5 h, and water was added to terminate the reaction. After that, it was extracted with ethyl acetate for three times, and the extract was dried with anhydrous sodium sulfate, filtered, and the solvent was removed under reduced pressure. Finally, a yellow solid product was obtained through rapid column chromatography with a silica gel column (eluent: ethyl acetate:petroleum ether=1:10), with a yield of 55%; the theoretical molecular formula and main nuclear magnetic testing data of the prepared product were as follows. Through analysis, it could be seen that the actual synthesized product is consistent with the theoretical analysis.

At room temperature, $[(Me_3Si)_2N]_3La(\mu\text{-}Cl)Li(THF)_3$ (21.1 mg, 0.024 mmol, 10 mol %) and toluene (0.1 mL) were weighed into a reaction flask after dehydration and deoxygenation treatment under argon protection for conventional mixing for 10 minutes, then diethyl phosphite (Compound 2, 37 μL, 0.29 mmol), isatin (N-ethyl isatin, 0.29 mmol) and toluene (0.3 mL) were added for conventional stirring and mixing for 30 min, and then toluene (0.6 mL) and 2,3-diphenylcyclohexanone (Compound 3, 50 mg, 0.24 mmol) were added and stirred at 110° C. for 2.5 h, and water was added to terminate the reaction. After that, it was extracted with ethyl acetate for three times, and the extract was dried with anhydrous sodium sulfate, filtered, and the solvent was removed under reduced pressure. Finally, a yellow solid product was obtained through rapid column chromatography with a silica gel column (eluent: ethyl acetate:petroleum ether=1:10), with a yield of 48%; the theoretical molecular formula and main nuclear magnetic testing data of the prepared product were as follows. Through analysis, it could be seen that the actual synthesized product is consistent with the theoretical analysis.

At room temperature, $LaCl_3$ (0.024 mmol, 10 mol %), $L_1$ (0.024 mmol) and toluene (0.1 mL) were weighed into a reaction flask after dehydration and deoxygenation treatment under argon protection for conventional mixing for 10 minutes, then diethyl phosphite (Compound 2, 37 μL, 0.29 mmol), isatin (N-ethyl isatin, 0.29 mmol) and toluene (0.3 mL) were added for conventional stirring and mixing for 30 min, and then toluene (0.6 mL) and 2,3-diphenylcyclohexanone (Compound 3, 50 mg, 0.24 mmol) were added and stirred at 110° C. for 2.5 h, and water was added to terminate the reaction. After that, it was extracted with ethyl acetate for three times, and the extract was dried with anhydrous sodium sulfate, filtered, and the solvent was removed under reduced pressure. Finally, there was no product obtained through rapid column chromatography with a silica gel column (eluent: ethyl acetate:petroleum ether=1:10), with a yield of 0.

Extended Example 3: at room temperature, $[(Me_3Si)_2N]_3Yb(\mu\text{-}Cl)Li(THF)_3$ (0.024 mmol, 10 mol %), $L_1$ (9.7 mg, 0.024 mmol) and toluene (0.1 mL) were weighed into a reaction flask after dehydration and deoxygenation treatment under argon protection for conventional mixing for 10 minutes, then diethyl phosphite (Compound 2, 37 μL, 0.29 mmol), isatin (N-ethyl isatin, 0.29 mmol) and toluene (0.3 mL) were added for conventional stirring and mixing for 30 min, and then toluene (0.6 mL) and 2,3-diphenylcyclohexanone (Compound 3, 50 mg, 0.24 mmol) were added and stirred at 110° C. for 2.5 h, and water was added to terminate the reaction. After that, it was extracted with ethyl acetate for three times, and the extract was dried with anhydrous sodium sulfate, filtered, and the solvent was removed under reduced pressure. Finally, a yellow solid product was obtained through rapid column chromatography with a silica gel column (eluent: ethyl acetate:petroleum ether=1:10), with a yield of 62%; the theoretical molecular formula and main nuclear magnetic testing data of the prepared product were as follows. Through analysis, it could be seen that the actual synthesized product is consistent with the theoretical analysis.

The pyrano[2,3-b]indol-2-one skeleton is a very important structural unit that widely exists in natural products and pharmaceutical molecules, and has certain biological activity. Therefore, studying the efficient synthesis techniques of pyrano[2,3-b]indol-2-one skeleton has important theoretical and practical significance.

The invention claimed is:

1. A method for reacting an isatin with a cyclopropenone compound at low catalytic amount, comprising the following steps: using a silicon amino rare earth compound as a catalyst for reacting the isatin with the cyclopropenone compound in an organic solvent in the presence of an amine compound and a phosphite ester; the chemical structural formula of the silicon amino rare earth compound is as follows

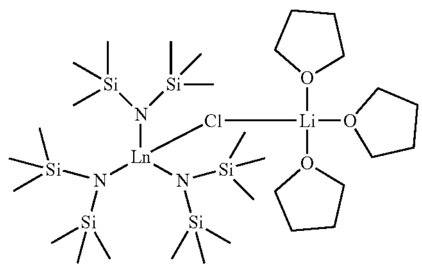

wherein: Ln is a trivalent rare earth metal ion;

the chemical structural formula of the amine compound is as follows:

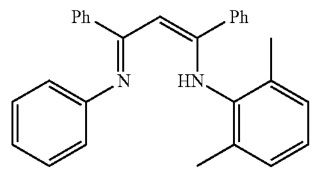

the general structure of the isatin is as follows:

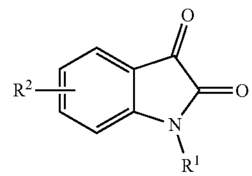

wherein: $R^1$ is selected from the group consisting of allyl, benzyl, ethyl, methyl, and acetyl; $R^2$ is selected from the group consisting of chlorine, fluorine, bromine, methyl, methoxy, nitro, trifluoromethyl, and trifluoromethoxy;

the general structure of the cyclopropenone is as follows:

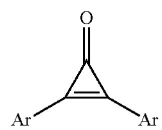

wherein: Ar is selected from the group consisting of phenyl, 4-methylphenyl, 4-fluorophenyl, and 4-chlorophenyl.

2. The method according to claim 1, wherein a molar ratio of the catalyst to the amine compound is range from 1:1 to 1:3.

3. The method according to claim 1, wherein the organic solvent is selected from the group consisting of 1,4-dioxane, ethylene glycol dimethyl ether, tetrahydrofuran, 1,2-dichloroethane, chlorobenzene, toluene, and n-hexane; the isatin reacts with the cyclopropenone compound under anhydrous and anaerobic conditions; the phosphite ester is diethyl phosphite.

4. The method according to claim 1, wherein by moles, an amount of the isatin is 1.2 times that of the cyclopropenone compound; an amount of the silicon amino rare earth compound is 10% of the cyclopropenone compounds.

5. The method according to claim 1, wherein: a product of the reaction between the isatin and the cyclopropenone compound is a pyrano[2,3-b]indol-2-one compound.

6. The method according to claim 1, wherein a reaction temperature is from 100° C. to 120° C.; a reaction time is from 2 hours to 3 hours.

7. The method according to claim 1, wherein mixing the silicon amino rare earth compound and the amine compound in the organic solvent; then mixing the phosphite ester, the isatin and the organic solvent for reaction, and then the cyclopropenone compound and the organic solvent are added for reaction.

* * * * *